(12) United States Patent
Ahmad (10) Patent No.: US 9,298,884 B1
(45) Date of Patent: Mar. 29, 2016

(54) REMOTE INSTRUCTION AND MONITORING OF HEALTH CARE

(71) Applicant: VITAAX LLC, Bedford, MA (US)

(72) Inventor: Talal Ali Ahmad, Bedford, MA (US)

(73) Assignee: Vitaax LLC, Bedford, MA (US)

( * ) Notice: Subject to any disclaimer, the term of this patent is extended or adjusted under 35 U.S.C. 154(b) by 0 days.

(21) Appl. No.: 14/573,176

(22) Filed: Dec. 17, 2014

(51) Int. Cl.
*G06F 19/00* (2011.01)
*G06K 9/62* (2006.01)
*G06T 15/00* (2011.01)

(52) U.S. Cl.
CPC .......... *G06F 19/3418* (2013.01); *G06K 9/6202* (2013.01); *G06T 15/00* (2013.01)

(58) Field of Classification Search
None
See application file for complete search history.

(56) References Cited

U.S. PATENT DOCUMENTS

| | | | |
|---|---|---|---|
| 2011/0238079 A1* | 9/2011 | Hannaford et al. ........... | 606/130 |
| 2012/0022408 A1* | 1/2012 | Hubschman ......... | A61B 3/0025 |
| | | | 600/587 |
| 2013/0172731 A1* | 7/2013 | Gole .............................. | 600/424 |
| 2013/0196300 A1* | 8/2013 | Huang et al. .................. | 434/262 |
| 2013/0308827 A1* | 11/2013 | Dillavou et al. .............. | 382/107 |
| 2014/0272866 A1* | 9/2014 | Kim .............................. | 434/262 |

OTHER PUBLICATIONS

A video showing a University of Alabama at Birmingham surgical team performing surgery using augmented reality technology from VIPAAR in conjunction with Google Glass. Video available at http://vimeo.com/77714943 and more information at http://www.vipaar.com/.
Touch Surgery surgical simulation software is an interactive surgical simulator that guides users step-by-step through an operation. More information at https://www.touchsurgery.com/ and the software is available at https://itunes.apple.com/gb/app/touchsurgery/id509740792.
Resolution Tube software provides an augmented reality interface to share video and allow drawing on the video. More information at http://www.resolutiontube.com/ and software available at https://play.google.com/store/apps/details?id=com.resolutiontube.resolutiontubeapp.

* cited by examiner

*Primary Examiner* — Stephen R Koziol
*Assistant Examiner* — Raphael Schwartz
(74) *Attorney, Agent, or Firm* — O'Neill Patent Law (57) ABSTRACT

Remote instruction and monitoring of health care may be facilitated by transmitting and processing image data of a patient, image data demonstrating a medical procedure, and image data of performance of the medical procedure. Image data of a patient may be transmitted to a remote doctor. Remote doctor may view the image data of the patient and provide a demonstration of a medical procedure. Image data of the demonstration may be provided to a local doctor who may perform the medical procedure. Image data of the performance of the procedure may be compared with image data of the demonstration of the procedure, and a result of the comparison may be transmitted to local doctor or remote doctor.

20 Claims, 6 Drawing Sheets

REMOTE INSTRUCTION AND MONITORING OF HEALTH CARE

BACKGROUND

Access to health care may be challenging for people based on the location where they live. For example, a person who lives far from a city may have to spend a prohibitive amount of time to travel to meet with a doctor. Further, even people who live near a city may not have easy access to a desired doctor. For example, a person may need a certain type of specialist who is not present in that city or may desire to meet with a specific doctor in another location.

Access to health care may be facilitated using telemedicine where doctors meet with patients using a phone, videoconference, or other communication techniques made possible by the Internet. In some situations, augmented reality techniques may be used to facilitate communication with a doctor over long distance.

In one example, augmented reality may be used to allow a remote surgeon to assist a local surgeon (local to the patient). Each of the local and remote surgeons may be able to view a video of the surgical site. Another camera may capture the remote surgeon's hand and may superimpose the video of the remote surgeon's hand onto the video of the surgical site. As the remote surgeon moves his hand, this movement may be reflected in the superimposed video, and both the remote and local surgeon may see the remote surgeon's hand in the video. The superimposed video may give the appearance of the remote surgeon interacting with the surgical site even though the remote surgeon may be 1000 miles away.

While telemedicine and augmented reality allow greater access to health care, a remote doctor may be able to provide even better care through additional technologies not provided by current augmented reality systems.

BRIEF DESCRIPTION OF THE FIGURES

The invention and the following detailed description of certain implementations thereof may be understood by reference to the following figures.

DETAILED DESCRIPTION

Described herein are techniques for facilitating the instruction and monitoring of healthcare by a remote doctor. While telemedicine and augmented reality provide some information to the remote doctor, the remote doctor can provide improved care if he is able to receive additional information about the patient, provide instructions that are more precise than pointing and speaking, and monitor the specific actions performed by a local doctor. Some examples of additional techniques that may be used include constructing three-dimensional (3D) representations of a patient, using 3D computer models of body parts to facilitate communication, and capturing a demonstration of a technique performed by a remote doctor and superimposing the demonstration on the patient.

For example, suppose a specific medical procedure to be performed comprises making an incision. The patient may be in a hospital bed and ready to undergo the procedure. Images or video of the surgical site on the patient may be captured. From these video or images, data may be provided to the remote doctor. The data could be, for example, the video or images, a 3D representation of the surgical site, or a 3D computer model of the body part where the incision is to be performed. Using this data, the remote doctor can provide instructions as to how to properly perform the incision. The remote doctor may, for example, draw on the provided data or simulate the incision using the provided data and augmented reality techniques. Images or video of the remote doctor providing the instructions may be captured and transmitted to the local doctor. The local doctor may be able to view the instructions superimposed on a live video of the patient and then perform the incision. Images or video of the local doctor performing the incision may be captured and compared with the instructions to provide feedback to both the local and remote doctors and determine if the local doctor has performed the procedure correctly.

For simplicity, the techniques will be described below with reference to a remote doctor assisting a local doctor, but the techniques are not limited specifically to doctors. For example, the remote person could be a nurse or other health care professional, and the local person could be the patient, a local nurse, or another local person without medical training who is providing health care to the patient. In addition, the techniques may be applied to veterinary care for animals as well as health care for people. The remote doctor may be a remote veterinarian, and the local doctor may be a local veterinarian providing care to an animal.

Figure 1:
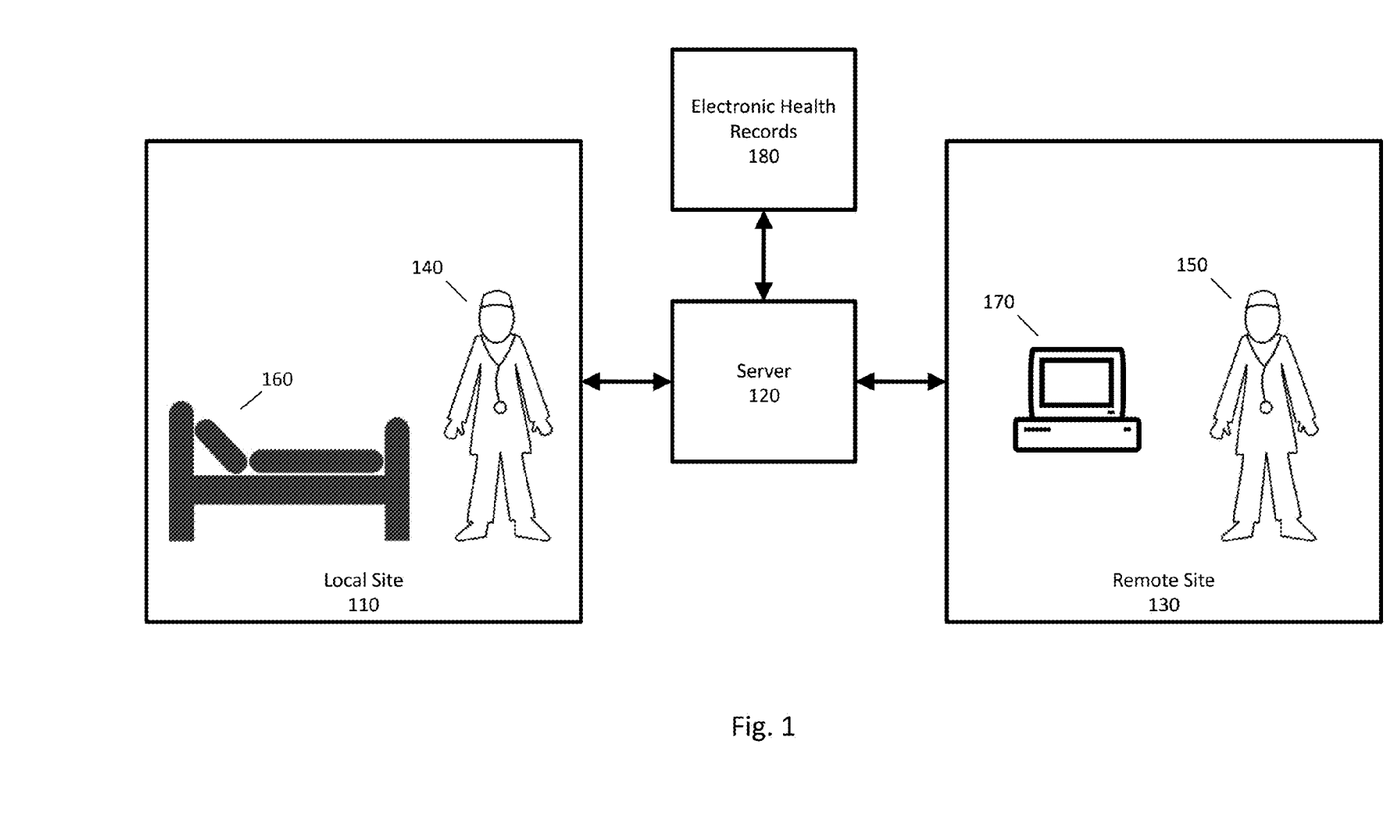
FIG. 1 illustrates one example of a system for allowing remote instruction and monitoring of health care.

FIG. 1 illustrates one example of a system for providing remote instruction and monitoring of health care. In FIG. 1, local doctor 140 (or other person) may be providing medical care to patient 160 at local site 110, and remote doctor 150 may be assisting local doctor 140 from remote site 130. Local site 110 may be far from remote site 140 such that it is not practical for patient 160 to travel to see remote doctor 150 in person. Local site 110 and remote site 130 may communicate with one another using any known networking techniques, including but not limited to telephone, email, videoconference, and the Internet (e.g., IPV4, IPV6, TCP, UDP, HTTP HTTPs, SNMP, DSCP, and SSL). In some implementations, server 120 may facilitate communications between local site 110 and remote site 130. In addition, any of local site 110, server 120, and remote site 130 may be connected to electronic health records 180. Electronic health records may be stored at local site 110, remote site 130, or any other suitable location. In some implementations, more than one remote site 130 may be in communication with local site 110. Although the description below refers to a single remote site 130, the techniques may also be applied with more than one remote site 130.

Figure 2:
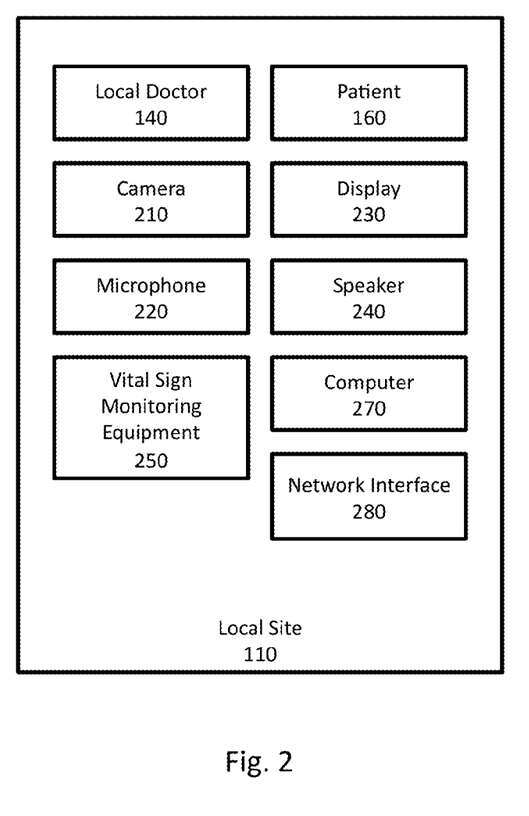
FIG. 2 illustrates components of one implementation of a local site where a patient may receive health care from a remote doctor.

FIG. 2 illustrates people and equipment that may be present in one example implementation of local site 110. As noted above, local doctor 140 and patient 160 may be present at local site 110, and other people may also be present to assist with medical care. Local site 110 may include any equipment that may be used by a doctor for treating a patient, such as vital sign monitoring equipment 250.

Local site 110 may include at least one camera 210 to allow remote doctor 150 to view local site 110. As used herein, camera may include device that takes pictures or any device that takes video (e.g., Wi-Fi or USB connected cameras and videocameras). At least one camera 210 may be directed to different locations in local site 110, including but not limited to the surgical site, to other portions of the patient's body (e.g., the face), and to local doctor 140. In some implementations, multiple cameras may point to the same location to allow for the construction of 3D image data as discussed in greater detail below. In some implementations, remote doctor 150 may be able to control the direction of camera 210. Local site 110 may also include at least one microphone 220 to allow remote doctor 150 to hear audio and conversations at local site 110. In some implementations, a microphone array may be used to allow remote doctor 150 to receive a better quality audio signal. Local site 110 may include at least one display 230 and at least one speaker 240 to allow people at local site 110 to see and hear remote doctor 150.

Local site 110 may also include at least one computer 270 that may be used to communicate with remote site 130 and to communicate with any other equipment and people at local site 110. Computer 270 may be a general-purpose computer or may be a specialized computer for use with telemedicine, and may communicate with remote site 130 using network interface 280. In one implementation, computer 270 may receive video from camera 210, audio from microphone 220, and vital sign information from vital sign monitoring equipment 250, and transmit this information to remote site 130. Computer 270 may also receive video, audio, and other information from remote site 130 and cause this information to be displayed or presented on other equipment at local site 110.

Audio and video transmitted between local site 110 and remote site 130 may use any known encoding and compression techniques (e.g., NTSC, PAL, H.264, SIP, H.323, G.711, G.726, AAC, and triple streaming encoder). Separate network connections may be used for any of video, audio, and other data, and the different network connections may have different priority levels to give priority to one type of data over other types of data. Network connections may use encryption techniques (e.g., SSL) for additional security.

The equipment described above is just one example of equipment that may be present at local site 110, and other equipment and other configurations of equipment are possible. For example, some of the equipment described above (e.g., camera 210, microphone 220, display 230, and speaker 240) may be part of computer 270 and need not be separate devices.

Figure 3:
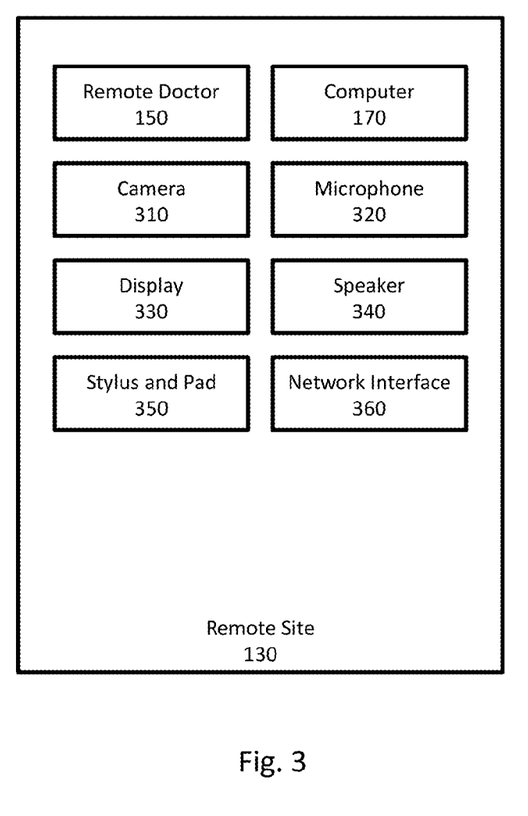
FIG. 3 illustrates components of a remote site from which a doctor may provide health care.

FIG. 3 illustrates people and equipment that may be present in one example implementation of remote site 130. As noted above, remote doctor 150 is present at remote site 130, and other people may also be present to assist with medical care. Remote site 130 may include any equipment that may be used by remote doctor 150 for treating a patient. Remote site 130 may have computer 170 to allow remote doctor 150 to communicate with local site 110. Computer 170 may be a general-purpose computer or a specialized computer for use with telemedicine. Computer 170 may communicate with local site 110 using network interface 360.

Remote site 130 may have one or more of any of a camera 310, a display 330, a microphone, 320, and a speaker 340 for communicating with local site 110. Each of these components may be part of computer 170 or separate devices from computer 170. Remote site 130 may have any specialized equipment to assist remote doctor 150 in communicating with local site. For example, remote site 130 may have a stylus and pad 350 to assist remote doctor 150 in presenting written or drawn information, or may have a 3D display and 3D glasses to allow remote doctor 150 to more easily view 3D data. In some implementations, remote site 130 may have multiple cameras so that 3D images of remote doctor 150 may be constructed and multiple microphones to generate a better quality audio signal.

Local site 110 and remote site 140 allow remote doctor 150 to instruct and monitor health care at local site 110. In some implementations, server 120 may be used as well, and server 120 is described in greater detail below. Before the beginning of a telemedicine session, each of local site 110 and remote site 130 may be set up with the proper equipment and the schedules of the needed people may be arranged. At the beginning of the telemedicine session, a connection may be made between local site 110 and remote site 130. Any number of connections may be made using any known connection techniques. For example, a videoconference may be initiated so that each of local site 110 and remote site 130 can see and hear what is going on at the other site, and this videoconference may be ongoing for the duration of the telemedicine session. In addition, information regarding the vital signs of patient 160 may be transmitted to remote site 130 for the duration of the telemedicine session. In one implementation, the videoconference and the vital signs are presented on a display of computer 170 at remote site 130.

During the telemedicine session, images, video, 2D or 3D illustrations, and other information may be communicated from local site 110 to remote site 130. Remote doctor 150 receives this information, and provides instructions for use by local doctor 150 at local site 110. Local doctor 140 may then perform an action to implement these instructions at local site 110. While local doctor 140 is performing the action, information about the performance of the action can be transmitted to remote doctor 150 so that remote doctor 150 can assess whether the instructions are being implemented correctly. Further, information about the performance of the action can be automatically compared against the instructions to determine whether local doctor 140 is implementing the instructions correctly. The automatic comparing of the action against the instructions may be performed, for example, by computer 270 at local site 110, server 120, computer 170 at remote site 130, or by another computer.

Figure 4A:
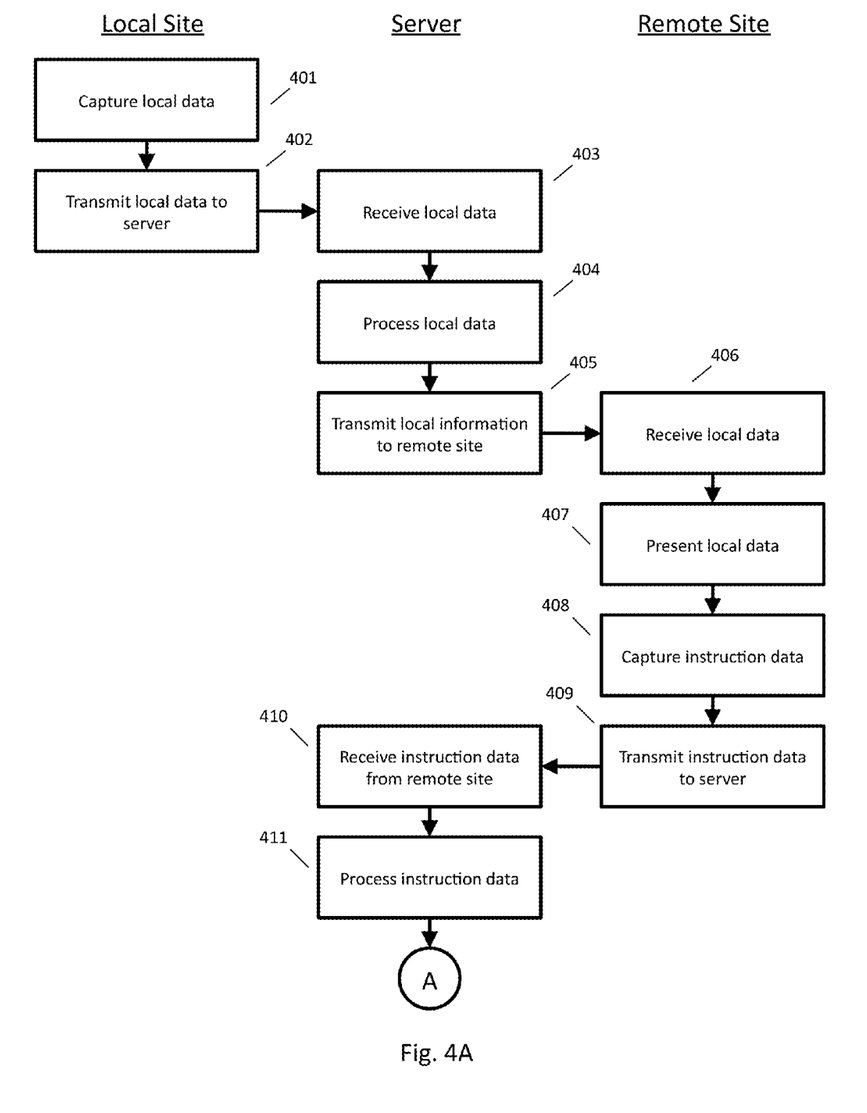
FIGS. 4A and 4B are flowcharts of an example process for providing remote instruction and monitoring of health care.
Figure 4B:
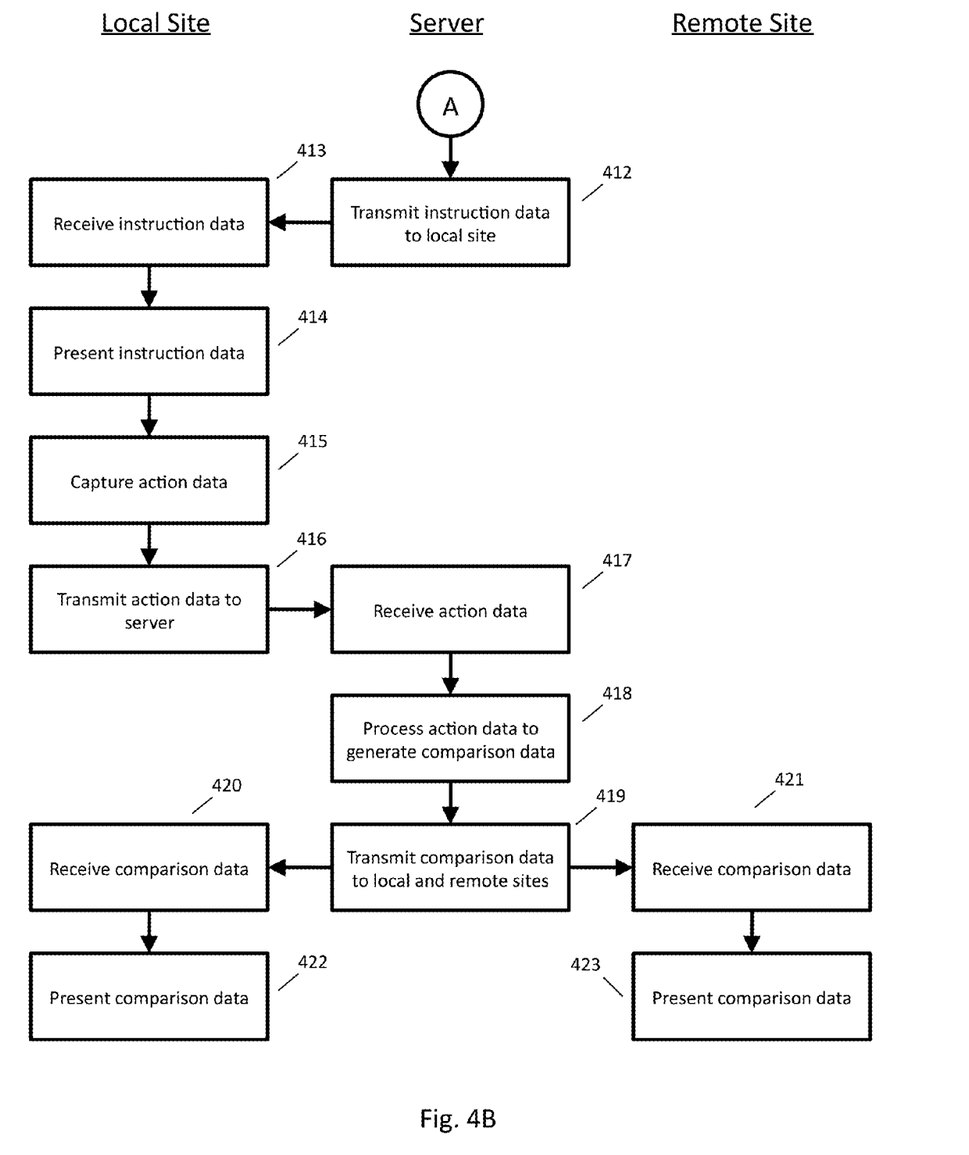

FIGS. 4A and 4B are flowcharts showing an example implementation of a process for allowing a remote doctor 150 to provide instruction and monitoring of health care at local site 110. Note that the ordering of the steps of FIGS. 4A and 4B is exemplary and that other orders are possible. The process of FIGS. 4A and 4B may be implemented simultaneously with a videoconference between local site 110 and remote site 130, the provision of vital signs to remote site 130, and other communication between local site 110 and remote site 130.

At step 401, local data is captured at local site 110. Local data may include any data obtained from local site 110 that may be used to assist remote doctor 150 in providing medical care and may include raw and/or processed data. The local data may include image data of a surgical site, of other portions of patient 160, or of other locations at local site 110. As used herein, image data may include any combination of pictures, images, and/or video, and image data may be 2D or 3D. The image data may be a conventional RGB (red, green, blue) image, an infrared image, a depth image (e.g., from a time-of-flight camera or a structured light camera), or any other type of image. In some implementations, multiple cameras may be directed to the same location so that the multiple images of a location may be used to reconstruct a 3D representation of the location. Local data may also include audio data of sounds and conversations at local site 110. The audio data may include multiple channels generated by an array microphone or by multiple microphones. Local data may also include vital signs received from vital sign monitoring equipment 250.

At step 402, the local data is transmitted to server 120, and at step 403, the server receives the local data. Note that, as described elsewhere herein, server 120 may not be used in all implementations and that the operations of server 120 may be performed at local site 110 or remote site 130.

At step 404, server 120 may process the local data. The processing of the local data may remove data, add data, and/or modify data. In some implementations, only some of the local data may be processed. For example, where the local data includes vitals signs, the vital signs may not need to be processed and this portion of the local data may not be modified. In some implementations the local data received from local site 110 may be raw data that is less useful for obtaining useful information about local site 110, and server 120 may process the local data to include more useful information. For example, a depth image of local site may be combined with an RGB camera image to generate a 3D image for remote doctor 150.

In some implementations, server 120 may perform one or more of the following operations in processing the local data: (i) generate a 3D representation of an object (e.g., the surgical site) using image data from multiple cameras and using techniques known to one of skill in the art, (ii) merge or fuse a depth image with an image that does not include depth to obtain a 3D representation of an object, (iii) obtain a 3D computer model of body part (either selected automatically or selected manually) and combine the computer model with a 3D image of the patient, (iv) adapt or warp a 3D computer model of a body part (either selected automatically or selected manually) so that it better matches the corresponding body part of the patient, (v) determine measurements (e.g., length) of portions of a representation of a patient and/or add a graphical representation (e.g., a ruler) to the image data to indicate the scale or length of the portions, (vi) apply audio signal processing techniques, such as beamforming, acoustic echo cancellation, noise reduction, and sound source localization to improve audio quality, or (vii) perform automatic speech recognition and/or natural language understanding on the received audio data. At step 405, the local data (as potentially modified by server 103) is transmitted to remote site 130, and at step 406, the local data is received at remote site 130.

Some aspects of steps 401-406 may be performed continuously and other aspects of steps 401-406 may be performed on request. For example, in some implementations, steps 401-406 may be performed continuously to create a 3D representation of patient 160 so that remote doctor 150 always has an up to date 3D view of patient 160. In some implementations, combining or adapting a computer model of a body part with the 3D representation of patient 160 may be performed on request. In some implementations, local doctor 140 or remote doctor 150 may take a snapshot (2D or 3D) of a representation of patient 160 and this snapshot may be used for generating 3D representations or combining or adapting a computer model of a body part with the 3D representation of patient 160.

At step 407, the local data is presented to remote doctor 150, such as by presenting the local data on a display of computer 170. An example of a user interface is described in greater detail below. For example, remote doctor 150 may be presented with 2D or 3D image data corresponding to local site 110, audio from local site 110, a display of patient information (e.g., name, age, height, and weight), and real time vital signs. In some implementations, (i) remote doctor 150 may be able to control the direction of cameras at local site 110 to change the view on his screen, (ii) may be able to rotate 2D or 3D images or video streams to obtain a different view, (iii) a 3D computer model of a body part may be presented to remote doctor 150, which may be rotated, scaled, or otherwise manipulated by remote doctor 150, or (iv) remote doctor 150 may be able to take snapshots of the live video so that he or she may examine them more closely or provide annotations, and the snapshots may be presented in a different portion of the user interface.

After reviewing the local information, remote doctor 150 may provide information about a medical procedure for local doctor 140. In addition to speaking with local doctor 140 on a videoconference, remote doctor 150 may annotate or draw on images or video and may demonstrate with his or her hands the medical procedure to be performed on patient 160. For example, remote doctor 150 may instruct local doctor 140 to perform a specific incision with a scalpel or to apply a suture.

Remote doctor 150 may demonstrate the medical procedure using a variety of techniques including one or more of the following: (i) drawing (such as drawing a line indicating an incision) on a 2D or 3D image/video of patient 160, (ii) drawing (such as drawing a line indicating an incision) on a 3D computer model of a body part, (iii), demonstrating the medical procedure on a 2D or 3D image/video of patient 160, or (iv) demonstrating the medical procedure on a 3D computer model of a body part.

To demonstrate the medical procedure, remote doctor 150 may draw on a display using his or her finger on a touch screen, use a mouse, use a stylus, or use any other techniques to draw on a display. Remote doctor may also draw using augmented reality. For example, a camera may be focused on a hand of remote doctor 150 and a video of the doctor's hand may be superimposed on 2D or 3D image data of patient 160 or on a 3D computer model of a body part. As the doctor draws, another image may be created corresponding to the drawing and this image may be superimposed with other image data to show the drawing. The drawing may simulate an action to be performed with a surgical tool, such as making an incision with a scalpel, and the speed of the drawing may be relevant in addition to the location of the drawing.

Remote doctor 150 may demonstrate the medical procedure using augmented reality. Remote doctor 150 may use only his hand or may hold medical tools, such as a scalpel. The doctor may virtually perform the action on 2D or 3D image data of patient 160 or on a 3D computer model of a body part. A display may show an image/video of the surgical site or the 3D computer model of the body part, and a camera may be focused on a hand of remote doctor 150. The video of the remote doctor's hand may be superimposed on image data of the surgical site or 3D computer model so that it appears that remote doctor 150 is actually performing the medical procedure on the surgical site or on the 3D computer model. For example, remote doctor 150 may be demonstrating an incision with a scalpel. The doctor's hand with the scalpel may appear in the image/video of the surgical site. As the tip of the scalpel comes in virtual contact with the patient's skin, the tip of the scalpel may disappear to simulate the scalpel cutting into the skin.

Remote doctor 150 may demonstrate the medical procedure using a data glove (i.e., a virtual/augmented reality glove, wired glove, or cyber glove). A data glove may include sensors to determine locations and movements of the hand and fingers. Data received from the data glove may be used to construct a 3D computer model of the remote doctor's hand, and the 3D computer model of the remote doctor's hand may be combined with image data of the patient so that remote doctor 150 may simulate performance of the medical procedure using the data glove.

During step 408, instruction data is obtained by computer 170 at remote site 130. The instruction data may include any data that may be beneficial for demonstrating to local doctor 140 how to perform the medical procedure. For example, where remote doctor 150 is drawing, the instruction data may include an image corresponding to the doctor's drawing or a video showing the doctor performing the drawing. Where remote doctor 150 is demonstrating the medical procedure on image data of the patient or on a computer model, the instruction data may include image data of the doctor virtually performing the medical procedure. The instruction data may also include timing data. For example, the drawing of the mark may simulate an incision with a scalpel and the action may preferably be done at a specified rate. Instruction data may also include other data provided by remote doctor 150, such as through a user interface on the computer or through speaking (which may be processed with speech recognition). For example, where the drawing corresponds to an incision, remote doctor 150 may type or speak a depth for the incision.

The instruction data may include raw and/or processed data. For example, where remote doctor 150 makes a drawing, the instruction information may include raw data corresponding to the doctor's placement of his or her finger on a touch screen at different times or may include a combined image data corresponding to the drawing on the image data of the patient or on the 3D computer model of the body part. Where the remote doctor performs an action using augmented reality, the instruction information may include the raw video taken of the doctor's hand, may include processed video, or may include information extracted from the video.

Where remote doctor 150 demonstrates the medical procedure using a virtual reality technique, the instruction data may include any data needed to construct a virtual reality representation of remote doctor 150 demonstrating the medical procedure on the patient. For example, the instruction data may include a video of the doctor's hand demonstrating the medical procedure against a green (or other color) background so the video of the doctor's hand may be combined with other image data (e.g., using chroma key techniques). While remote doctor 150 is demonstrating the medical procedure, he may be viewing a live video showing the augmented reality representation combination of the video of his hand with image data of the patient, and the instruction data may include this combined video.

At step 409, the instruction data is transmitted to server 120, and at step 410, the instruction data is received by server 120. At step 411, server 120 may process the instruction data to remove data, add data, or modify data. In one implementation, server 120 may process the instruction data to determine the values of relevant parameters relating to the performance of the medical procedure. For example, the instruction data may be processed to determine the location on the patient where the incision started, a path of the incision on the patient, the location on the patient where the incision ended, a depth of the incision at one or more locations, a width of the incision, or a speed of the incision at one or more locations. In another example, where the medical procedure is placing a suture, the entry location, exit location, and depth may be recorded for each stitch.

In one implementation, server 120 may process the instruction data to generate and include a replayable video of remote doctor 150 demonstrating the medical procedure. The replayable video may present the values of parameters relating to the instruction. For example, the replayable video may include a graphic indicating the length of an incision, the depth of the incision (which may vary across the incision), and the speed at which the incision was made. By replaying the video, local doctor 140, may be able to better understand the remote doctor's instruction.

In some implementations, server 120 may combine the instruction data with a current video of patient 160. Remote doctor may have created the instruction using first image data of patient 160, and patient 160 may have since moved since remote doctor 150 demonstrated the medical procedure. Server 120 may modify the instruction data so that it matches current image data of patient 160. For example, server 120 may compare first image data of patient 160 to current image data of patient 160 to determine a change in position of patient 160. The comparison may be done by comparing feature points from the first image data and the current image data. The feature points could be physical features on the patient, features physical drawn on the patient using ink or infrared ink, or any other relevant features. The comparison may be done in two dimensions or three dimensions. After the comparison is made, the instruction data may be modified (e.g., scaled, translated, or rotated) so that it correctly presents the demonstration of the medical procedure on the current image data of the patient. In some implementations, the current image data may be processed in near real time as any movement of the patient occurs.

Where remote doctor 150 demonstrates the medical procedure using a 3D computer model of a body part, server 120 may transform the instruction data so that it matches current image data of patient 160. For example, feature points of patient 160 can be matched to feature points of the 3D computer model and a transformation may be applied to obtain the best fit between the patient and the 3D computer model. In some implementations, the current image data may be processed in near real time as any movement of the patient occurs.

At step 412, the instruction data (as potentially modified by server 120) is transmitted by server 120 to local site 110, and at step 413, the instruction information is received by local site 110. At step 414, local site 110 presents the instruction data. For example, where the instruction data includes a replayable video, a user interface accessible to local doctor 140 may include a control to allow local doctor 140 to replay the demonstration of the medical procedure by remote doctor 150. The replayable video may be shown on a display using augmented reality. For example, the display may show a live video of patient 160 and the replayable video may be superimposed on the live video. Local doctor 140 may be able to start, pause, stop, and replay the demonstration and view it on the live video of patient 160. Where the demonstration was provided using augmented reality, the replayable video may show remote doctor's hands demonstrating the medical procedure on a live video of patient 160. Where the demonstration was provided using a 3D computer model of a body part, the computer model may be visible in the replayable video. In some implementations, the 3D computer model may represent what the body part should like after the action is completed so local doctor 140 can see the current state of patient 160 and a representation of how patient 160 should appear after the medical procedure has been performed.

After local doctor 140 has reviewed the instruction data from remote doctor 150, he or she may be ready to perform the medical procedure according to the instruction. While local doctor 140 is performing the medical procedure, the performance of the medical procedure may be captured by cameras 210 at local site 110. Information corresponding to his or her performance of the medical procedure may be determined from image data and compared to the instructions provided by remote doctor 150. The results of the comparison may be presented to one or both of local doctor 140 and remote doctor 150 while local doctor 140 is performing the medical procedure. Accordingly, steps 415-423, described below, may be performed in a loop to provide continuous updates to local doctor 140 and remote doctor 150 while the medical procedure is being performed.

At step 415, action data is captured. Action data may include any information that may be used to evaluate the performance of the medical procedure by local doctor 140 and may be similar to or different from the instruction data of step 408. In some implementations, the action data may include image data of local doctor 140 performing the medical procedure. At step 416, the action data may be transmitted to server 120, and at step 417, the action data may be received by server 120.

At step 418, server 120 may compare the action data with the instruction data and generate comparison data that may indicate similarities and differences between the instruction data and the action data. In some implementations, the instruction data and the action data may be compared by computing values of one or more parameter. Parameters may include, for example, locations, depths, timing, or any other factor relevant to a medical procedure. For an incision, relevant parameters may include the start point, the path of the incision, the depth at different points along the path, and the speed of the incision. For a suture, relevant parameters may include, for each stitch of the suture, the input location, the output location, the depth, and the tension of the thread.

The parameters to be used for a medical procedure may depend on the specific medical procedure. In some implementations, the parameters (i) may be specified by the remote doctor, (ii) may be retrieved from a database that specifies relevant parameters for a variety or medical procedures, or (iii) may be determined automatically from the demonstration by remote doctor 150.

In some implementations, the parameter values may be determined from image data using techniques such as image processing, computer vision, and object recognition. For the instruction data, parameter values may be determined from image data of remote doctor 150 demonstrating the medical procedure. For the action data, parameter values may be determined from image data of local doctor 140 performing the medical procedure. In some implementations, the parameter values may be provided by remote doctor 150 in other ways. For example, remote doctor may speak or type into a user interface a desired depth of an incision.

Server 120 may create comparison data that may be used to present the comparison to local doctor 140 and remote doctor 150. In some implementations, the comparison data may include a graphical representation that is to be presented on top of image data of the patient. For example, a graphical representation indicating differences between the medical procedure as instructed and as performed. In some implementations, the comparison data may focus on the most important differences. For example, where differences in parameters of one part of an incision are small and differences in parameters for another part of an incision are large, the comparison data may only relate to the parameters with large differences.

For example, consider local doctor 140 performing an incision. The comparison data may include image data that indicates an instructed path of an incision (perhaps in one color) and the actual path of the incision (perhaps in another color). The comparison data may also include image data that indicates the instructed depth of the incision and the actual depth of the incision, for example as two line plots. This image data from the comparison data may be superimposed on image data of the patient or may be presented separately.

At step 419, server 120 transmits the comparison data to at least one of local site 110 and remote site 130. At steps 420 and 422, the local site 110 receives and presents the comparison data, and at steps 421 and 423, remote site 130 receives and presents the comparison data. After reviewing the comparison data, local doctor 140 may modify the course of performing the medical procedure or remote doctor 150 may provide verbal instruction to local doctor 140.

Where the medical procedure has been performed by local doctor 140 incorrectly, remote doctor 150 may again demonstrate the medical procedure and the process may return to step 401 and repeat itself. Where the action has been performed correctly, local doctor 140 and remote doctor 150 may proceed to the next stage of the surgical procedure and the process may return to step 401 for the next stage.

Figure 5:
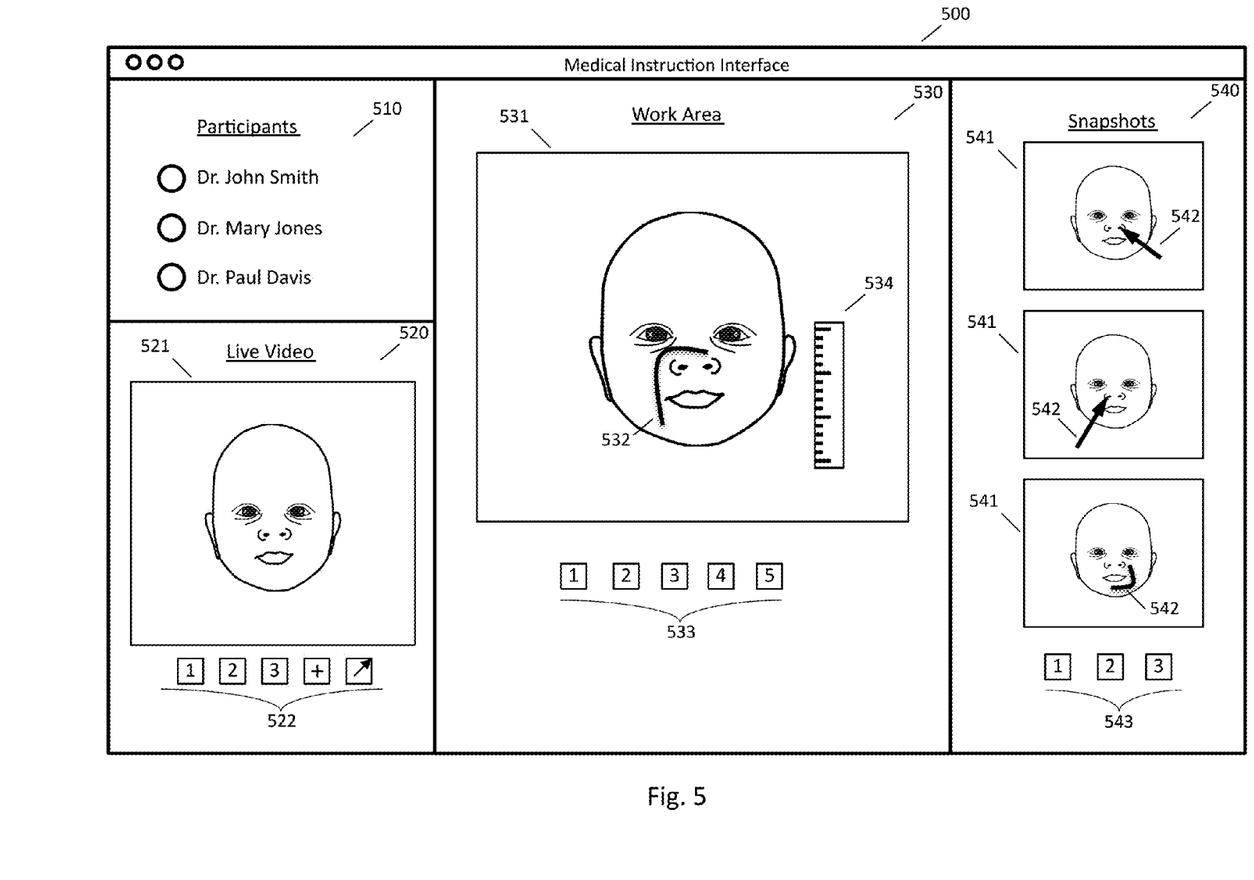
FIG. 5 illustrates an example user interface that may be used by a remote doctor to provide instruction and monitoring of health care.

FIG. 5 illustrates an example user interface 500 that may be used by remote 150 doctor to provide instruction and monitoring of health care. User interface 500 may appear on a display connected to computer 170 at remote site 130, which may be any type of computing device, including but not limited to a general-purpose personal computer. User interface 500 may be presented by software installed on computer 170 or may be generated by a remote computer and presented on the display, for example as a web page. Before arriving at user interface 500, remote doctor 150 may need to perform other actions, such as authentication or connecting to a particular network address. User interface 500 is just one example of a user interface that may be used, and the techniques described herein are not limited to any particular user interface.

User interface 500 may present different information in different portions of the screen. For example, user interface 500 may present a participant portion 510, which may present a list of people taking part in the telemedicine session. In addition to a list of names, any relevant information may be included, such as pictures, titles, location, and length of time since joining the session.

User interface 500 may also present a live video portion 520 showing a live video stream 521 (either 2D or 3D) from local site 110. Audio from local site 110 may also be played on speakers connected to computer 170. Remote doctor 150 may perform several actions relating to live video portion 520 using, for example, buttons 522. Remote doctor 150 may, for example, be able to (i) make live video stream 521 larger, (ii) make live video stream 521 fill the entire display, (iii) pause live video stream 521 to show a still image, (iv) take a snapshot of live video stream 521 (which may appear in work area portion 530 or snapshot portion 540), (v) select other video streams to display from local site (e.g., a live video stream of the patient from a different angle or a live video stream of local doctor 140, (vi) control the direction, zoom, or focus of the camera providing live video stream 521, (vii) make annotations directly on live video stream 521 (discussed in greater detail below, (viii) see annotations made by another person (such as local doctor 140), (ix) clear annotations from live video stream 521, (x) rotate or move a 3D representation of a patient or of a model of a body part to obtain a different perspective, (xi) add a graphical representation of a ruler that matches a scale of an object in live video stream 521, or (xii) add a 2D or 3D computer model of a body part and move, scale, rotate, and/or perform other transformations of the computer model to match the patient in live video stream 521.

Live video portion 520 may also show video streams created using augmented reality techniques, such as when remote doctor 150 demonstrates a medical procedure. In an augmented reality representation, image data from multiple sources may be combined and shown together as a single video stream. When creating an augmented reality representation of remote doctor 150 demonstrating a medical procedure, two kinds of image data may be used. The first may be image data (still images or video) of patient 160. The second may be image data of remote doctor 150 performing the demonstration of the medical procedure. Remote doctor 150 may be able to watch an augmented reality presentation in real time.

User interface 500 may also present a work area portion 530 where remote doctor 150 may perform annotations, such as annotation 532, of image data and other manipulations of image data. Work area portion 530 may include working image data 531, which may include any image data (e.g., still images or video) that remote doctor 150 would like to manipulate. Remote doctor 150 may manipulate working image data 531 using, for example, buttons 533. In one implementation, remote doctor 150 may be able to annotate working image data 531, for example, by drawing lines, arrows, or any other annotation. Remote doctor 150 may add the annotations using any known techniques for adding annotations to image data. Where remote doctor 150 is annotating video (such as live video stream 521) the annotations may track movement of the patient or the camera so if the patient moves or the camera moves or zooms, the annotations will automatically adapt to maintain the position of the annotation on the patient.

Remote doctor 150 may also perform other actions relating to working image data 531, such as (i) make working image data 531 larger, (ii) make working image data 531 fill the entire display, (iii) pause working image data 531 to show a still image, (iv) take a snapshot of working image data 531 (which may appear in snapshot portion 540), (v) select image data to present as working image data 531 (e.g., from live video stream 521 or snapshot portion 540), (vi) see annotations made by another person (such as local doctor 140), (vii) clear annotations, (viii) zoom in or out, (ix) rotate or move working image data 531 where it is a 3D representation of a patient or of a model of a body part to obtain a different perspective, (x) add a graphical representation of a ruler 534 that matches a scale of an object in working image data 531, or (xi) add a 2D or 3D computer model of a body part and move, scale, rotate, and/or perform other transformations of the computer model to match the patient in working image data 531.

User interface 500 may also present a snapshot portion 540 where remote doctor 150 may store snapshots 541 of image data. The snapshots may be still images or video segments and may have annotations, such as annotations 542, or be edited in other ways (e.g., zoomed into a portion of the image data). Remote doctor 150 may manipulate snapshots 541 using, for example, buttons 543. Remote doctor 150 may manipulate snapshots by deleting them, sharing them others (e.g., local doctor 140), or selecting them for editing or annotation.

Figure 6:
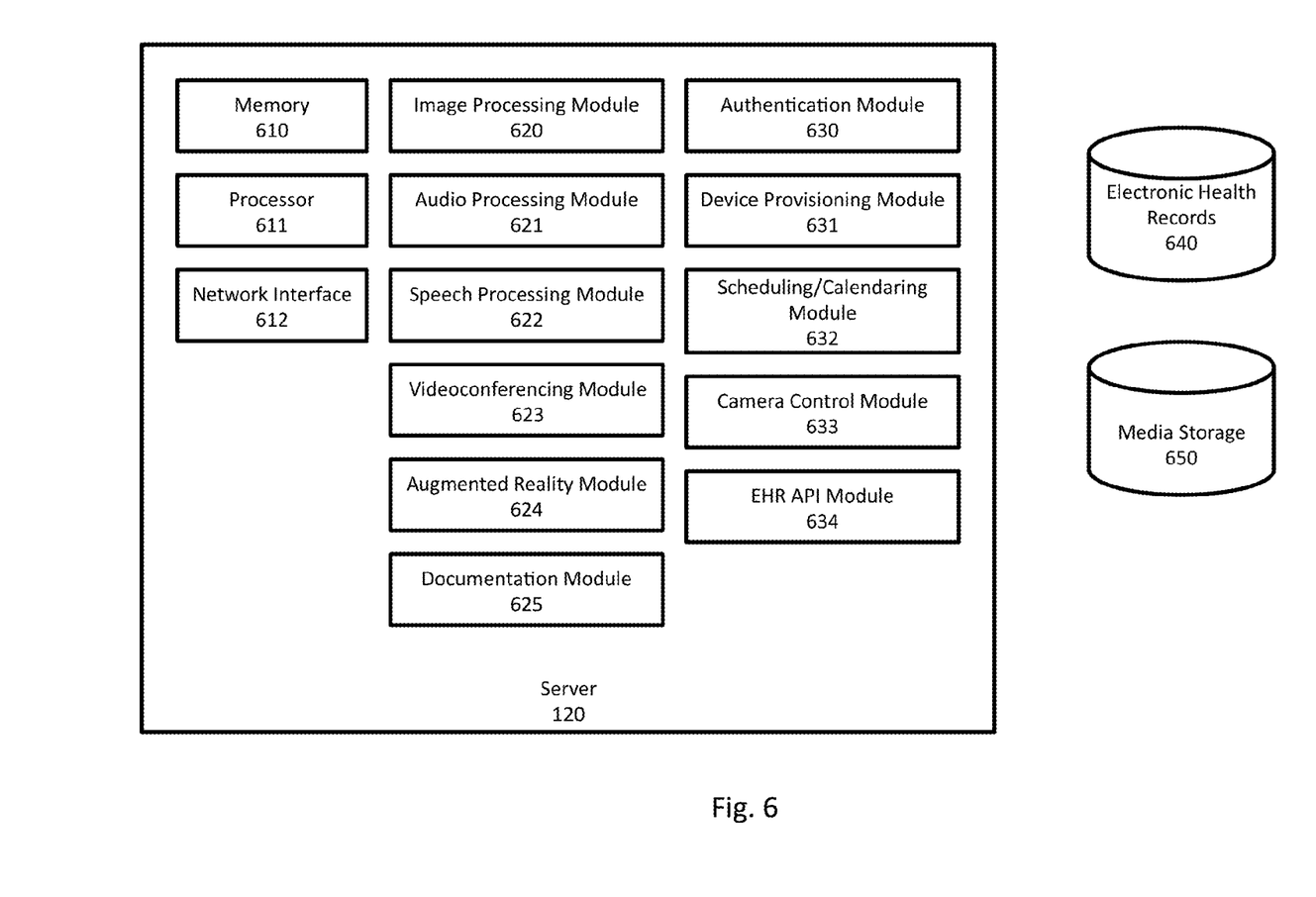
FIG. 6 illustrates components of a server that may be used to connect a local site to a remote site.

FIG. 6 illustrates an example implementation of server 120. As noted above, in some implementations, the operations of server 120 may be performed at local site 110, remote site 130, or elsewhere. Server 120 may comprise one or more computers, and different computers may perform different operations. For example, one computer may perform speech recognition and another computer may perform authentication.

Server 120 may be a general-purpose computer or may be a specialized computer for use with telemedicine. Server 120 may include any components typical of a computing device, such one or more processors 611, volatile or nonvolatile memory 610, and one or more network interfaces 612. Server 120 may also include any known input and output components, such as displays, keyboards, and touch screens. Server 120 may also include a variety of components or modules providing specific functionality, and these components or modules may be implemented in software, hardware, or a combination thereof. Below, several examples of components are described for one example implementation of server 120, and other implementations may include additional components or exclude some of the components described below.

Server 120 may include an image processing module 620. Image processing module 620 may by configured to perform any image processing related functions described above, including for example, creating 3D representations from multiple sets of image data, performing object recognition (e.g., body part or medical tool recognition), tracking objects in image data, and determining values for parameters such as the location or depth of an incision. Server may include an audio processing module 621 that may be configured to process one or more channels of audio data by performing techniques such as beamforming, acoustic echo cancellation, noise reduction, and sound source localization to improve audio quality. Server 120 may include a speech processing module 622 that may perform operations such as speech recognition and natural language understanding to understand spoken commands and other speech and to automatically take action in response to understood speech (e.g., to request the presence of another person in an emergency).

Server 120 may include a videoconferencing module 623 to facilitate a videoconference between local site 110 and remote site 130. Server 120 may include an augmented reality module 624 to create augmented reality representations from multiple sets of image data. Server 120 may include a documentation module 625 to record any relevant information to the performance of the medical procedure and store the relevant information at media storage 650. Media may be stored using any known encoding and compression techniques (e.g., MPEG-3 or MPEG-4). Stored media may be indexed and searchable (e.g., using the HL7 clinical documentation architecture or digital imaging and communications in medicine (DICOM)). For example, it may be desired to save some or all of audio and video transmitted between local site 110 and remote site 130, annotations created by local doctor 140 or remote doctor 150, augmented reality representations of remote doctor 150 demonstrating medical procedures, image data or audio data of local doctor 140 performing medical procedures, or any other relevant data. Such data may be stored, for example, for educational or insurance purposes.

Server 120 may include an authentication module 630 to authenticate local doctor 140, remote doctor 150, or other persons, and to facilitate network connections between local site 110 and remote site 130. Server 120 may include a device provisioning module 631 to facilitate the installation of software and other data on devices at local site 110 and remote site 130, such as the software that generates user interface 500. Server 120 may include a scheduling/calendaring module 632 to facilitate finding times available to local doctor 140, remote doctor 150, other persons, local site 110 and remote site 130. Server 120 may include a camera control module 633 that allows remote doctor 150 to control camera 210 at local site 110. Server 120 may include an electronic health record (EHR) API module 634 to interface with EHR 640, which may be stored in memory of server 120, may be stored in proximity to server 120, or may be stored in remote locations from server 120. EHR API module 634 may implement standards for accessing EHR, such as Health Level-7. EHR API module 634 may retrieve EHR stored at other locations and make it available to local doctor 140 and remote doctor 150.

The foregoing description describes telemedicine techniques to allow remote doctor 150 to assist local doctor 140 in performing a medical procedure, and examples include references to medical procedures relating to surgical procedures. The foregoing techniques, however, are not limited to surgical procedures and apply to any medical procedures and to any situation where a remote person is providing medical advice to another person. In another example, a remote person may be a physical therapist and the local person may be a patient receiving physical therapy. The remote physical therapist may guide the patient in performing various physical therapy procedures. The physical therapist may receive 2D or 3D image data of the patient and demonstrate physical therapy procedures. The demonstration of the physical therapy procedures may include any of the techniques described above, including creating an augmented reality representation of the physical therapist demonstrating a physical therapy technique on 2D or 3D image data of the patient.

The physical therapist may then monitor the patient performing the physical therapy procedures. Image data may be obtained of the patient performing the physical therapy procedures and values may be determined for various parameters. For example, a procedure may require the patient to bend his or her leg repeatedly between 45 and 90 degrees and the actual range of the leg bend may determined from the image data. The actual range of the leg bend may be reported to one or both of the patient or physical therapist. In another example, the patient may be connected to various sensors or wearable devices to provide additional data to the physical therapist. The sensors may includes sensors for pulse, temperature, and hydration and wearable devices may include fitness bands, watches, smart glasses, and smart phones.

Depending on the implementation, steps of any of the techniques described above may be performed in a different sequence, may be combined, may be split into multiple steps, or may not be performed at all. The steps may be performed by a general purpose computer, may be performed by a computer specialized for a particular application, may be performed by a single computer or processor, may be performed by multiple computers or processors, may be performed sequentially, or may be performed simultaneously.

The techniques described above may be implemented in hardware, in software, or a combination of hardware and software. The choice of implementing any portion of the above techniques in hardware or software may depend on the requirements of a particular implementation. A software module or program code may reside in volatile memory, nonvolatile memory, RAM, flash memory, ROM, EPROM, or any other form of a non-transitory computer-readable storage medium.

Conditional language used herein, such as, "can," "could," "might," "may," "e.g.," is intended to convey that certain implementations include, while other implementations do not include, certain features, elements and/or steps. Thus, such conditional language indicates that that features, elements and/or steps are not required for some implementations. The terms "comprising," "including," "having," and the like are synonymous, used in an open-ended fashion, and do not exclude additional elements, features, acts, operations. The term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is to be understood to convey that an item, term, etc. may be either X, Y or Z, or a combination thereof. Thus, such conjunctive language is not intended to imply that certain embodiments require at least one of X, at least one of Y and at least one of Z to each be present.

While the above detailed description has shown, described and pointed out novel features as applied to various implementations, it can be understood that various omissions, substitutions and changes in the form and details of the devices or techniques illustrated may be made without departing from the spirit of the disclosure. The scope of inventions disclosed herein is indicated by the appended claims rather than by the foregoing description. All changes which come within the meaning and range of equivalency of the claims are to be embraced within their scope.

What is claimed is:

1. A system for monitoring a medical procedure comprising a first computer at a first location, a second computer at a second location, and a server computer, wherein:
    the first computer is configured to obtain first image data of a patient and transmit the first image data to the server computer;
    the server computer is configured to process the first image data and transmit the processed first image data to the second computer;
    the second computer is configured to:
        cause the processed first image data to be presented on a second display,
        obtain second image data, wherein the second image data comprises instructions regarding performance of an incision, and
        receive data provided by a user, wherein the data comprises additional instructions regarding performance of the incision and wherein the data is not derived from image data;
        transmit the data provided by the user and the second image data to the server computer;
    the server computer is configured to process the second image data and transmit the processed second image data to the first computer;
    the first computer is configured to:
        cause the processed second image data to be presented on a first display,
        obtain third image data of the patient, wherein the third image data comprises an image of the incision being performed on the patient, and
        transmit the third image data to the server computer;
    the server computer is configured to:
        determine a first value of a first parameter from the second image data,
        determine a second value of the first parameter from the third image data,
        compare the first value and the second value,
        generate comparison data, and
        transmit the comparison data to the first computer and the second computer;
    the first computer is configured to cause the comparison data to be presented on the first display; and
    the second computer is configured to cause the comparison data to be presented on the second display.

2. The system of claim 1, wherein:
    the first image data comprises images from a plurality of cameras; and the server computer is configured to process the first image data to generate a 3D representation of at least a portion of the patient.

3. The system of claim 1, wherein:
the second image data comprises a video of a hand simulating the incision.

4. The system of claim 1, wherein:
the first computer is configured to obtain vital sign data of the patient and transmit the vital sign data to the server computer;
the server computer is configured to transmit the vital sign data to the second computer; and
the second computer is configured to cause the vital sign data to be presented on the second display.

5. The system of claim 1, wherein the first parameter comprises a starting location of an incision, an ending location of an incision, or a depth of an incision at a location.

6. The system of claim 1, wherein the comparison data comprises a graphical representation illustrating a difference between the first value and the second value.

7. The system of claim 1, wherein the second computer is configured to receive the data provided by the user by performing speech recognition on speech of the user.

8. A computer-implemented method for monitoring a medical procedure, the method comprising:
receiving first image data from a first location, wherein the first image data corresponds to a patient;
transmitting the first image data to a second location;
receiving second image data from the second location, wherein the second image data comprises instructions regarding performance of an incision;
receiving data provided by a user, wherein the data comprises additional instructions regarding performance of the incision and wherein the data is not derived from image data;
transmitting the second image data to the first location;
receiving third image data from the first location, wherein the third image data corresponds to the incision being performed on the patient;
determining a first value of a first parameter from the second image data;
determining a second value of the first parameter from the third image data;
comparing the first value and the second value; and
transmitting a result of the comparison to at least one of the first location or the second location.

9. The computer-implemented method of claim 8, wherein transmitting the first image data to the second location comprises:
determining a scale of an object in the first image;
modifying the first image data by combining the first image data with fourth image data, wherein the fourth image data comprises a graphical representation indicating the scale.

10. The computer-implemented method of claim 8, wherein the first image data comprises a plurality of pictures taken by a plurality of cameras, a plurality of videos taken by a plurality of cameras, or a 3D representation.

11. The computer-implemented method of claim 8, wherein transmitting the second image data to the first location comprises transmitting image data comprising a combination of (i) image data of a person demonstrating the incision and (ii) image data of the patient.

12. The computer-implemented method of claim 8, wherein the third image data comprises a video of a person performing the incision on the patient.

13. The computer-implemented method of claim 8, wherein the first parameter comprises a start location of a stitch, an end location of a stitch, or a depth of a stitch.

14. The computer-implemented method of claim 8, further comprising facilitating a videoconference between the first location and the second location.

15. One or more non-transitory computer-readable media comprising computer-executable instructions that, when executed by one or more computers, cause the one or more computers to perform actions comprising:
obtaining, by a first computer at a first location, first image data corresponding to a patient;
causing, by the first computer, transmission of the first image data to a second computer at a second location;
causing, by the second computer, presentation of first image data;
obtaining, by the second computer, second image data, wherein the second image data comprises instructions regarding performance of an incision;
receiving, by the second computer, data provided by a user, wherein the data comprises additional instructions regarding performance of the incision and wherein the data is not derived from image data;
causing, by the second computer, transmission of the data provided by the user and the second image data to the first computer;
causing, by the first computer, presentation of the second image data;
obtaining, by the first computer, third image data, wherein the third image data corresponds to the incision being performed on the patient;
obtaining, by the first computer, information about a comparison of the second image data and the third image data;
causing, by the first computer, presentation of the information about the comparison.

16. The one or more non-transitory computer-readable media of claim 15 wherein the actions further comprise:
transmitting, by the first computer, the third image data to a server computer;
receiving, by the first computer from the server computer, the information about the comparison;
receiving, by the second computer from the server computer, the information about the comparison; and
causing, by the second computer, presentation of the information about the comparison.

17. The one or more non-transitory computer-readable media of claim 15 wherein the information about the comparison comprises a graphical representation of a difference between a first value of a parameter determined from the second image data and a second value of the parameter determined from the third image data.

18. The one or more non-transitory computer-readable media of claim 15 wherein causing, by the first computer, transmission of the first image data to a second computer at a second location comprises:
transmitting, by the first computer, the first image data to a server computer, wherein the server computer modifies the first image data and transmits the modified first image data to the second computer.

19. The one or more non-transitory computer-readable media of claim 15 wherein the second image data comprises a 3D computer model of a body part.

20. The one or more non-transitory computer-readable media of claim 15 wherein causing, by the second computer, presentation of first image data comprises presenting a graphical representation indicating a scale of an object in the first image data.

* * * * *